United States Patent

Lafon

Patent Number: 5,621,011
Date of Patent: Apr. 15, 1997

[54] [α-TERT.BUTYL AMINOMETHYL)-3,4-DICHLOROBENZYL] THIOACETAMIDE, A PROCEDURE FOR ITS PREPARATION AND ITS USES

[75] Inventor: Louis L. Lafon, Paris, France

[73] Assignee: Laboratoire L. Lafon, Maisons Alfort, France

[21] Appl. No.: 496,452

[22] Filed: Jun. 29, 1995

Related U.S. Application Data

[62] Division of Ser. No. 186,877, Jan. 19, 1993, abandoned, which is a division of Ser. No. 542,948, Jun. 25, 1990, abandoned.

[30] Foreign Application Priority Data

Jun. 26, 1989 [FR] France ................... 89 08480

[51] Int. Cl.$^6$ ................... A61K 31/165
[52] U.S. Cl. ................... 514/618
[58] Field of Search ................... 514/618

[56] References Cited

U.S. PATENT DOCUMENTS

| | | | |
|---|---|---|---|
| 3,624,143 | 11/1971 | Shen et al. | 564/162 |
| 4,534,874 | 8/1985 | Steinberg et al. | 564/162 |
| 4,808,572 | 7/1989 | Beck et al. | 564/154 |
| 4,843,071 | 6/1989 | Hohenwarter | 514/217 |

FOREIGN PATENT DOCUMENTS 0158545   6/1985   European Pat. Off. .

*Primary Examiner*—Shailendra Kumar
*Attorney, Agent, or Firm*—Jacobson, Price, Holman & Stern, PLLC

[57] ABSTRACT

The invention relates to [α-(tert.butyl aminomethyl)-3,4-dichlorobenzyl] thioacetamide of the formula:

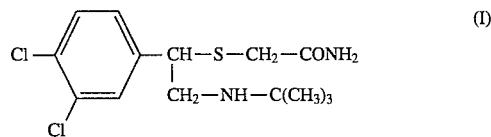

(I)

and its addition salts with pharmaceutically acceptable acids.

These compounds can be used as antidepressants as well as to promote the feed intake.

2 Claims, 1 Drawing Sheet

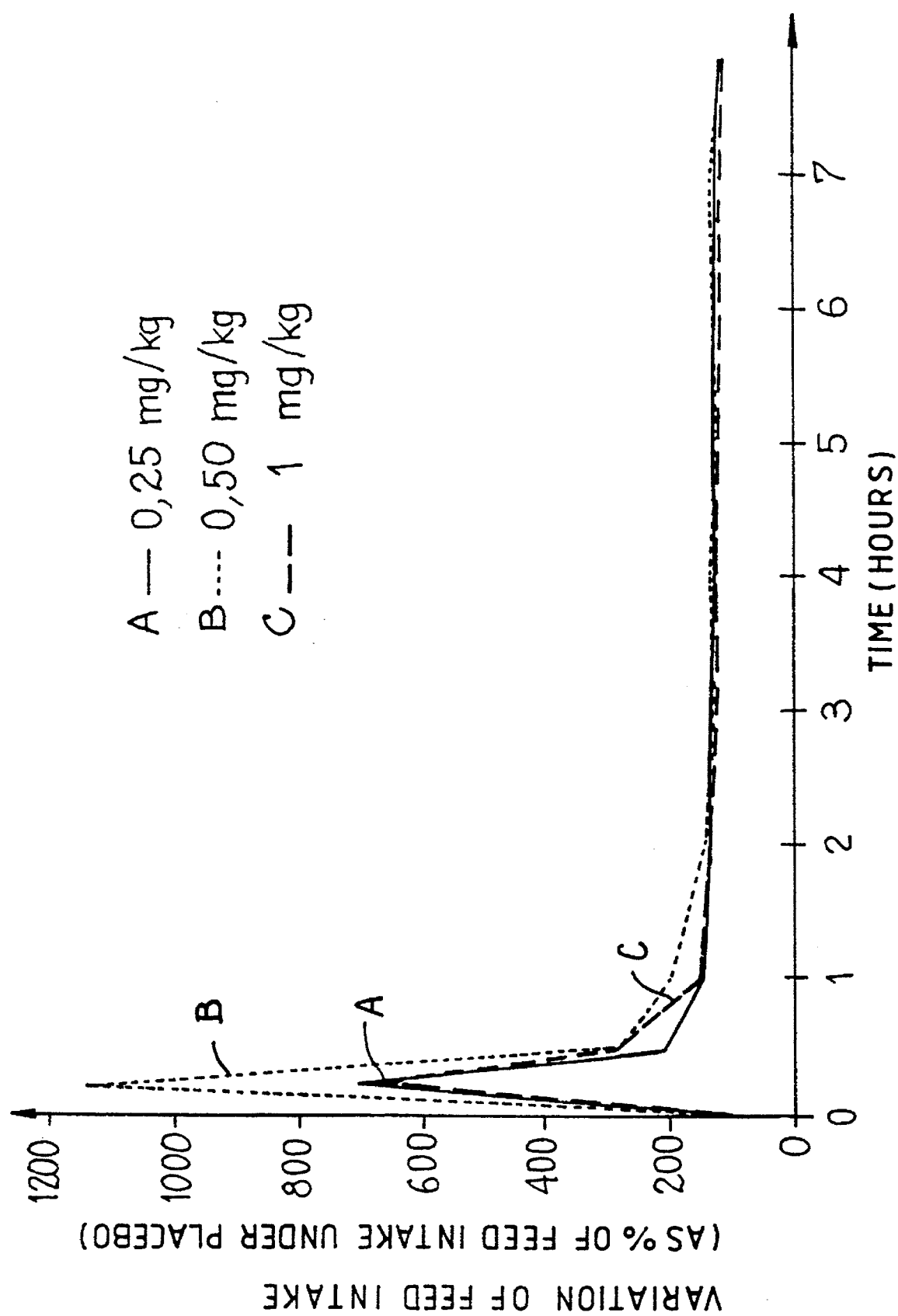

[α-TERT.BUTYL AMINOMETHYL)-3,4-DICHLOROBENZYL] THIOACETAMIDE, A PROCEDURE FOR ITS PREPARATION AND ITS USES

This is a divisional of application Ser. No. 08/186,877, filed Jan. 19, 1193, now abandoned which is a continuation of Ser. No. 07/542,948, filed Jun. 25, 1990 abandoned.

The present invention relates to new derivatives of α-aminomethyl-benzyl-thioacetic acid and, in particular, to new derivatives of α-aminomethyl-benzylthioacetamide.

Derivatives of α-aminomethyl-benzylthioacetic acid have already been described in EP-A-O-158 545. These compounds have an action on the central nervous system and can be used in therapy as antidepressants.

Derivatives of α-aminomethyl-benzylthioacetic acid have now been found which exhibit a distinctly more powerful action on the central nervous system.

Therefore, the present invention relates to [α-(tert.butyl aminomethyl) -3,4-dichlorobenzyl] thioacetamide of the formula:

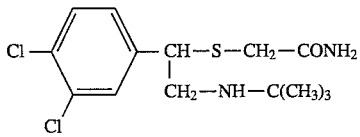

(I)

and its addition salts with pharmaceutically acceptable acids.

BRIEF DESCRIPTION OF THE DRAWING

FIG. 1 is a graph representing the data from animal tests.

The "addition salts with pharmaceutically acceptable acids" designate the salts which give the biological properties of the free bases without having an undesirable effect. These salts may be, in particular, those formed with mineral acids such as hydrochloric acid, hydrobromic acid, sulfuric acid, nitric acid, phosphoric acid; metal hydrogen salts such as disodium orthophosphate and monopotassium sulfate, and organic acids such as formic acid, acetic acid, propionic acid, glycolic acid, oxalic acid, fumaric acid, maleic acid, citric acid, malonic acid, methane sulfonic acid, lactic acid, succinic acid, tartaric acid.

The compound of formula I may be obtained by reaction of 1-(3,4-dichlorophenyL) 2-bromo- ethanol with tert.butylamine, the conversion of the aminoalcohol obtained into the aminochloro derivative, condensation of the aminochloro derivative with methyl thioglycolate and aminolysis of the ester thus obtained.

The following example illustrates the preparation of the compounds according to the invention.

EXAMPLE

Preparation of [α-(tert.butylaminomethyl) 3,4-dichlorobenzyl] thioacetamide hydrochloride (CRL 41 414).

1) Preparation of 2-(tert.butylamino)-1-(3,4-dichlorophenyl) ethanol hydrochloride.

60 g (0.22 mole) of 1-(3,4-dichlorophenyl)-2-bromoethanol dissolved in 200 ml of ethanol are added to a solution of 80 ml of tert.butylamine in 200 ml of ethanol. After 48 hours at 20° C. and 3 hours at reflux, the mixture is evaporated to dryness in a vacuum, taken up in N NaOH, extracted with ether, the ethereal extract is extracted with 2N HCl, precipitated with concentrated NaOH, filtered off, washed with water and dried. The base is obtained (m.p. =111° C.) in a yield of 80%; a solution of this latter in ethyl acetate is converted quantitatively into the hydrochloride by the addition of ethanolic hydrogen chloride (m.p. =210–211° C.).

2) Preparation of 2-(tert.butylamino)-1-(3,4-dichlorophenyl) 1-chloroethane hydrochloride.

29.85 g (0.1 mole) of the hydrochloride obtained in 1) in 120 ml of $CH_2Cl_2$ are treated with 20 ml of $SOCl_2$ in 50 ml of $CH_2Cl_2$; after 5 hours at reflux and being left to stand overnight, the product is filtered off, washed with ether and dried to give the chloro derivative in quantitative yield (m.p. =236°–238° C.).

3) Preparation of methyl, [α-(tert.butylaminomethyl)-3,4-dichlorobenzyl]thioacetate hydrochloride.

4.4 g (0.192 At-g) of sodium in 250 ml of methanol, 10 ml (0.1 mole) of methyl thioglycolate and 30.5 g (0.096 mole) of the hydrochloride of the chloro derivative obtained in 2) are mixed in the cold. After ½ hour at 20° C., the mixture is heated at reflux for 3 hours. The NaCl is filtered off, the filtrate is evaporated in vacuum, the residue s taken up in ether, washed with water, extracted with 100 ml of N HCl, precipitated in the cold with concentrated NaOH, extracted with ether, washed with water, dried, filtered, acidified with ethanolic hydrogen chloride, filtered off, washed with ether and ethyl acetate and dried. The hydrochloride of the ester is obtained in 68% yield (m.p. =154°–155° C.).

4) Preparation of [α-(tert.butylaminomethyl)-3,4-dichlorobenzyl] thioacetamide hydrochloride.

15.9 g (0.04 mole) of the hydrochloride obtained in (3) dissolved in 200 ml of methanol are treated with 80 ml of 28% ammonia.

After reaction for 24 hours, the alcohol is evaporated, 50 ml of N HCl are added, the solution is filtered through charcoal, precipitated with concentrated NaOH, extracted with ether, dried, filtered and acidified with ethanolic hydrogen chloride, filtered off, washed with ethyl acetate and recrystallized from acetone.

The compound is obtained in a yield of 42%.

It is a white powder, soluble in water and alcohols; insoluble in ether and ethyl acetate.

It melts at 176° C.

Pharmacological and toxicological results are given below demonstrating the advantages of he compound (CRL 41 414) according to the invention compared with the compounds described in EP-A-O 158 545.

The compound which was described in EP-A-O 158 545 and which is structurally very similar to the compound according to the invention, namely [α-(isopropyl-aminomethyl) 3,4-dichlorobenzyl] thioacetamide fumarate (CRL 41253) is used as reference compound.

1) Toxicity

A pre-toxicity study was carried out in the mouse by the i.p. route.

a) CRL 41 414

No mortality at 128 mg/kg. At 256 mg/kg, convulsions are observed leading to death within 15 minutes (3 animals out of 3).

b) CRL 41 253

No mortality at 256 m/k but convulsions in 1 mouse out of 3. At 512 mg/kg, sedation is observed followed by convulsions leading to death (3 animals out of 3).

Thus, CRL 41 253 is at best, two times less toxic than CRL 41 414.

2) Antagonism of the hypothermias induced by apomorphine, reserpine and oxotremorine in the mouse (i.p. administration of the compounds tested)

|  | CRL 41 414 | CRL 41 253 |
| --- | --- | --- |
| Apomorphine 16 mg/kg | 1 mg/kg +++ | 32 mg/kg + |
| Reserpine 2.5 mg/kg | 1 mg/kg + | 32 mg/kg + |
| Oxotremorine 0.5 mg/kg | 1 mg/kg + | 32 mg/kg + |

(In this table, + indicates the threshold of an effect whereas +++ represents a very marked effect).

These results demonstrate the activity of CRL 41 414 at doses 32 times lower than that of CRL 41 253 in these tests which are standard tests for the demonstration of an antidepressant effect.

3) Action on behavioural despair

One half-hour after the test substance had been administered by the i.p. route to groups of 6 mice, the mice are placed in a trough full of water. The decrease of immobility under the effect of the test substance is determined.

|  | CRL 41 414 | CRL 41 253 |
| --- | --- | --- |
| Minimal dose diminishing the duration of immobility | 4 mg/kg | 32 mg/kg |

The results demonstrate an effect of CRL 41 414 at doses 8 times lower than the reference compound in this test which confirms the antidepressant effect of CRL 41 414.

4) Action on barbiturate sleep

One half-hour after the administration of the test substance by the i.p. route, groups of mice receive an intraperitoneal injection of barbital (220 mg/kg).

The minimal dose which decreases the duration of barbiturate sleep is determined.

|  | CRL 41 414 | CRL 41 253 |
| --- | --- | --- |
| Minimal dose | 4 mg/kg | 32 mg/kg. |

This test demonstrates a stimulant effect at a dose of 4 mg/kg for the compound according to the invention.

The present invention relates also to therapeutic compositions containing as active ingredient [α-(tert.butyl aminomethyl) 3,4-dichlorobenzyl] thioacetamide or one of its addition salts with pharmaceutically acceptable acids.

The therapeutic compositions according to the invention may be administered to man or animals by the oral or parenteral routes.

They may be in the form of solid, semi-solid or liquid preparations. As examples may be mentioned tablettes, capsules, suppositories, injectable solutions or suspensions as well as sustained-release forms and implanted slow-release forms.

In these compositions, the active ingredient is usually mixed with one or more common, pharmaceutically acceptable excipients well known to the person skilled in the art.

The amount of active ingredient administered obviously depends on the patient who is being treated, the route of administration and the severity of the disease.

Furthermore, it has been discovered that the compound according to the invention stimulates feed intake in animals and hence can be used to promote appetite in man and animals.

Furthermore, results of a study performed in the rat on the effect of the compound according to the invention on feed intake will be given below.

Sprague Dawley male rats, 80 days old and weighing on average 374 g when weight measurements were begun, were used in the study. These rats were placed in individual cages 22 days before measurements were begun. The animals were fed ad libitum with the diet Extralabo M20 and had free access to water throughout the study. The animals were conditioned to a light-dark cycle comprising 8 h of darkness and 16 h of light. The test substance dissolved in physiological saline (0.9% NaCl) as well as a placebo constituted by physiological saline were administered by the intraperitoneal route in a volume of 1 ml/kg.

The results are presented in the only appended figure in which the variation of food intake as a percentage of the food intake under placebo is shown as a function of time.

In this figure, the curve A corresponds to a dose of 0.25 mg/kg, curve B to a dose of 0.50 mg/kg and curve C to a dose of 1 mg/kg.

With the compound of formula I an increase in food intake is observed which is 7 to 11 times higher than that observed in the absence of the administration of the compound of formula I.

Hence, the present invention relates also to a composition promoting the feed intake in man and animals and which contains as active ingredient the compound of formula I. The present invention finds an application in the feeding of livestock such as cattle or poultry for which the composition of the invention provides in particular an increase of the weight intake.

For the animal feeding the composition may take the form, in particular, of a premix containing the active ingredient dispersed in a vehicle or diluent or also the form of a feed supplement containing the active ingredient mixed with a vehicle or diluent.

In these last two cases, the vehicle is preferably a constituent of animal feed, such as oats, soy-bean seeds, alfalfa, wheat, fermentation residues, ground oyster shells, molasses, edible plant substances, soy-bean flower, kaolin, talc, crushed limestone, etc...

In the form of a premix, compositions according to the invention intended to promote the animal feeding may contain from 10 to 80% by weight of the compound of formula I or one of its non-toxic salts and from 90 to 20% by weight of the vehicle or diluent. These premixes may be diluted with a feed supplement for animals or may be added directly to an animal feed ration so as to provide an appropriate feed.

Alternatively, the compound of formula I and its non-toxic salts may be administered in the form of a solution or suspension containing an efficacious amount of this active ingredient in the animals' drinking water.

An appropriate amount supplied in this manner may vary from 0.0005 to 0.05% by weight of the amount of the daily feed of the animals.

I claim:

1. A method for promoting appetite in humans and animals comprising administering to a human or an animal an effective amount of [α-(tert.butyl aminomethyl)-3,4-dichlorobenzyl] thioacetamide having the formula

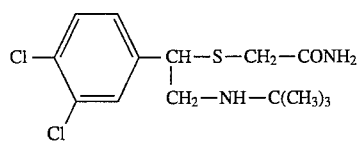
(I)
or a pharmaceutically acceptable acid-addition salt thereof.
2. A method for making an animal feed that promotes feedintake comprising adding to animal feed a feed-promoting effective amount of [α-(tert.butyl aminomethyl)-3,4-dichlorobenzyl] thioacetamide having the formula
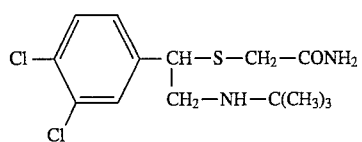
(I)
or a pharmaceutically acceptable acid-addition salt thereof.
* * * * *